United States Patent
Galeano Nunez et al.

(10) Patent No.: US 10,710,054 B2
(45) Date of Patent: Jul. 14, 2020

(54) MULTI-ZONED CATALYST SYSTEM FOR OXIDATION OF O-XYLENE AND/OR NAPHTHALENE TO PHTHALIC ANHYDRIDE

(71) Applicant: BASF SE, Ludwigshafen (DE)

(72) Inventors: Diana Carolina Galeano Nunez, Mannheim (DE); Christian Walsdorff, Ludwigshafen (DE); Jürgen Zühlke, Speyer (DE); Hans-Martin Allmann, Neunkirchen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/545,532

(22) PCT Filed: Jan. 14, 2016

(86) PCT No.: PCT/EP2016/050601
§ 371 (c)(1),
(2) Date: Jul. 21, 2017

(87) PCT Pub. No.: WO2016/116340
PCT Pub. Date: Jul. 28, 2016

(65) Prior Publication Data
US 2018/0008962 A1    Jan. 11, 2018

(30) Foreign Application Priority Data

Jan. 22, 2015    (EP) .................................... 15152057

(51) Int. Cl.
*B01J 23/22* (2006.01)
*B01J 35/00* (2006.01)
(Continued)

(52) U.S. Cl.
CPC ............. *B01J 23/22* (2013.01); *B01J 21/063* (2013.01); *B01J 23/002* (2013.01); *B01J 23/18* (2013.01);
(Continued)

(58) Field of Classification Search
CPC ........ B01J 23/22; B01J 21/063; B01J 23/002; B01J 23/18; B01J 27/198; B01J 35/0006;
(Continued)

(56) References Cited

U.S. PATENT DOCUMENTS

| | | |
|---|---|---|
| 5,169,820 A | 12/1992 | Ueda et al. |
| 6,362,345 B1 | 3/2002 | Heidemann et al. |

(Continued)

FOREIGN PATENT DOCUMENTS

| | | |
|---|---|---|
| AU | 2003281997 A1 | 2/2004 |
| CN | 1302294 A | 7/2001 |

(Continued)

OTHER PUBLICATIONS

WO 2004/103943 Machine Translation (Year: 2004).*

(Continued)

*Primary Examiner* — James A Fiorito
(74) *Attorney, Agent, or Firm* — Faegre Drinker Biddle & Reath LLP

(57) ABSTRACT

The present invention relates to a catalyst system for oxidation of o-xylene and/or naphthalene to phthalic anhydride (PA) comprising at least four catalyst zones arranged in succession in the reaction tube and filled with catalysts of different chemical composition wherein the active material of the catalysts comprise vanadium and titanium dioxide and the active material of the catalyst in the last catalyst zone towards the reactor outlet has an antimony content (calculated as antimony trioxide) between 0.7 to 3.0 wt. %. The present invention further relates to a process for gas phase (Continued)

oxidation in which a gas stream comprising at least one hydrocarbon and molecular oxygen is passed through a catalyst system which comprises at least four catalyst zones arranged in succession in the reaction tube and filled with catalysts of different chemical composition wherein the active materials of the catalysts comprise vanadium and titanium dioxide and the active material of the catalyst in the last catalyst zone towards the reactor outlet has an antimony content (calculated as antimony trioxide) between 0.7 to 3.0 wt. %.

19 Claims, 1 Drawing Sheet

(51) Int. Cl.
  *B01J 37/02* (2006.01)
  *B01J 23/00* (2006.01)
  *B01J 27/198* (2006.01)
  *B01J 35/10* (2006.01)
  *B01J 23/18* (2006.01)
  *B01J 21/06* (2006.01)
  *C07C 51/265* (2006.01)
  *C07C 51/31* (2006.01)
  *B01J 37/08* (2006.01)
  *C07D 307/89* (2006.01)
  *B01J 35/02* (2006.01)

(52) U.S. Cl.
  CPC ......... *B01J 27/198* (2013.01); *B01J 35/0006* (2013.01); *B01J 35/1004* (2013.01); *B01J 37/0219* (2013.01); *B01J 37/0221* (2013.01); *B01J 37/0236* (2013.01); *B01J 37/08* (2013.01); *C07C 51/265* (2013.01); *C07C 51/313* (2013.01); *C07D 307/89* (2013.01); *B01J 35/023* (2013.01); *B01J 35/026* (2013.01); *B01J 35/1014* (2013.01); *B01J 37/0223* (2013.01); *B01J 2523/00* (2013.01)

(58) Field of Classification Search
  CPC ............ B01J 35/1004; B01J 37/0219; B01J 37/0221; B01J 37/0236; B01J 37/08; C07C 51/265; C07C 51/313; C07D 307/89
  See application file for complete search history.

(56) References Cited

U.S. PATENT DOCUMENTS

| | | | |
|---|---|---|---|
| 6,586,361 B1 | 7/2003 | Heidemann et al. |
| 7,371,893 B2 | 5/2008 | Storck et al. |
| 7,618,918 B2 | 11/2009 | Estenfelder et al. |
| 7,687,425 B2 | 3/2010 | Storck et al. |
| 8,097,558 B2 | 1/2012 | Estenfelder et al. |
| 8,796,173 B2 | 8/2014 | Wölk et al. |
| 9,061,988 B2 | 6/2015 | Welker-Nieuwoudt et al. |
| 9,169,188 B2 | 10/2015 | Macht et al. |
| 9,238,217 B2 | 1/2016 | Welker-Nieuwoudt et al. |
| 9,656,983 B2 | 5/2017 | Kramer et al. |
| 9,695,099 B2 | 7/2017 | Liu et al. |
| 9,700,876 B2 | 7/2017 | Macht et al. |
| 9,714,227 B2 | 7/2017 | Zakzeski et al. |
| 9,765,046 B2 | 9/2017 | Fischer et al. |
| 2009/0306409 A1 | 12/2009 | Gückel et al. |
| 2011/0124885 A1 | 5/2011 | Altwasser et al. |
| 2014/0213801 A1 | 7/2014 | Altwasser et al. |
| 2015/0246343 A1 | 9/2015 | Hammon et al. |
| 2016/0145226 A1 | 5/2016 | Fischer et al. |
| 2016/0152530 A1 | 6/2016 | Grune et al. |
| 2016/0152531 A1 | 6/2016 | Walsdorff et al. |
| 2016/0347686 A1 | 12/2016 | Grune et al. |
| 2016/0355450 A1 | 12/2016 | Grune et al. |
| 2017/0008866 A1 | 1/2017 | Fischer et al. |
| 2017/0008867 A1 | 1/2017 | Galeano Nunez et al. |
| 2017/0121534 A1 | 5/2017 | Tavares Andre et al. |
| 2017/0233313 A1 | 8/2017 | Grune et al. |

FOREIGN PATENT DOCUMENTS

| | | |
|---|---|---|
| CN | 101939104 A | 1/2011 |
| CN | 103025424 A | 4/2013 |
| DE | 4006935 A1 | 9/1991 |
| DE | 19839001 A1 | 3/2000 |
| EP | 522871 A1 | 1/1993 |
| EP | 1636161 A1 | 3/2006 |
| JP | 2003-012664 A | 1/2003 |
| JP | 2008-531633 A | 8/2008 |
| WO | WO-2004014819 A2 | 2/2004 |
| WO | WO-2004103561 A1 | 12/2004 |
| WO | WO-2004103943 A1 | 12/2004 |
| WO | WO-2005115615 A1 | 12/2005 |
| WO | WO-2006125467 A1 | 11/2006 |
| WO | WO-2010022830 A2 | 3/2010 |
| WO | WO-2011032658 A1 | 3/2011 |
| WO | WO 2012014154 | 2/2012 |
| WO | WO 2014207603 A2 | 12/2014 |

OTHER PUBLICATIONS

U.S. Appl. No. 61/761,812, filed Feb. 7, 2013.
U.S. Appl. No. 61/822,950, filed May 14, 2013.
U.S. Appl. No. 61/878,651, filed Sep. 17, 2013.
U.S. Appl. No. 61/945,845, filed Feb. 28, 2014.
U.S. Appl. No. 14/277,414, filed May 14, 2014.
U.S. Appl. No. 62/086,236, filed Dec. 2, 2014.
U.S. Appl. No. 15/525,330, filed May 9, 2017.
European Search Report for EP Application No. 15152057, dated Aug. 11, 2015.
Golunski, S., "Antimony Oxides: a Guide to Phase Changes During Catalyst Preparation", Applied Catalysis, 1989, vol. 48, Issue 1, pp. 123-135.
Rosowski, F., et al., "New silver- and vanadium-containing multimetal oxides for oxidation of aromatic hydrocarbons", Catalysis Today, 2010, vol. 157, Issues 1-4, pp. 339-344.
Schubert, U.-A., et al., "Possible effects of site isolation in antimony oxide-modified vanadia/titania catalysts for selective oxidation of o-xylene", Topics in Catalysis, 2001, vol. 15, No. 2-4, pp. 195-200.
International Preliminary Examination Report for PCT/EP2016/050601 dated May 8, 2017.
International Search Report for PCT/EP2016/050601 dated May 30, 2016.

* cited by examiner

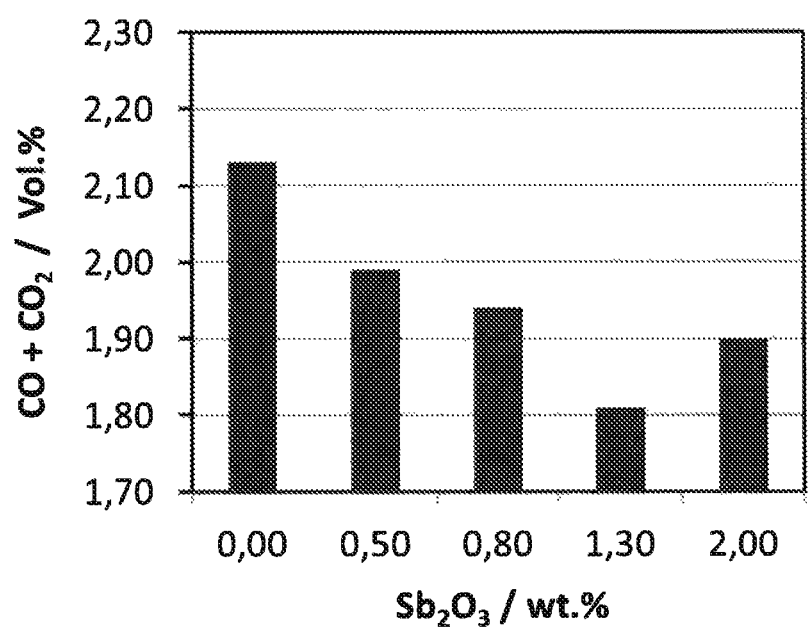

MULTI-ZONED CATALYST SYSTEM FOR OXIDATION OF O-XYLENE AND/OR NAPHTHALENE TO PHTHALIC ANHYDRIDE

CROSS-REFERENCE TO RELATED APPLICATIONS

This application is a national stage application (under 35 U.S.C. § 371) of PCT/EP2016/050601, filed Jan. 14, 2016, which claims benefit of European Application No, 15152057.4, filed Jan. 22, 2015, both of which are incorporated herein by reference in their entirety.

The present invention relates to a catalyst system for oxidation of o-xylene and/or naphthalene to phthalic anhydride (PA) comprising at least four catalyst zones arranged in succession in the reaction tube and filled with catalysts of different chemical composition wherein the active material of the catalysts comprises vanadium and titanium dioxide and the active material of the catalyst in the last catalyst zone towards the reactor outlet has an antimony content (calculated as antimony trioxide) between 0.7 to 3.0 wt. %. The present invention further relates to a process for gas phase oxidation in which a gas stream comprising at least one hydrocarbon and molecular oxygen is passed through a catalyst system which comprises at least four catalyst zones arranged in succession in the reaction tube and filled with catalysts of different chemical composition wherein the active material of the catalysts comprises vanadium and titanium dioxide and the active material of the catalyst in the last catalyst zone towards the reactor outlet has an antimony content (calculated as antimony trioxide) between 0.7 to 3.0 wt. %.

A multitude of carboxylic acids and/or carboxylic anhydrides is prepared industrially by the catalytic gas phase oxidation of hydrocarbons such as benzene, the xylenes, naphthalene, toluene or durene in fixed bed reactors. In this way, it is possible to obtain, for example, benzoic acid, maleic anhydride, phthalic anhydride, isophthalic acid, terephthalic acid or pyromellitic anhydride. In general, a mixture of an oxygen-containing gas and the starting material to be oxidized is passed through reactor tubes containing a bed of a catalyst. For temperature regulation, the tubes are surrounded by a heat carrier medium, for example a salt melt.

Useful catalysts for these oxidation reactions have been found to be what are called coated catalysts, in which the catalytically active material has been applied in the form of a shell on an inert carrier material such as steatite. In general, the catalysts have a layer of active material which has been applied in the form of a shell with essentially homogeneous chemical composition. In addition, it is also possible for two or more different active materials to be applied successively to a carrier. In that case, the reference is made to a two-shell or multi-shell catalyst (see, for example, DE 19839001 A1).

The catalytically active constituents used in the catalytically active material of these coated catalysts are generally titanium dioxide and vanadium pentoxide. In addition, small amounts of a multitude of other oxidic compounds which influence the activity and selectivity of the catalyst as promoters may be present in the catalytically active material, including cesium oxides, phosphorus oxides and antimony oxides.

The catalytic gas-phase oxidation of o-xylene or/and naphthalene for the production of phthalic anhydride (PA) is carried out on a large scale in chemical industry. Catalysts giving a particularly high PA yield can be obtained according to EP 1636161 when specific $V_2O_5/Sb_2O_3$ ratios are established and the antimony trioxide has a defined median particle size. In this case, the presence of antimony oxides leads to an increase in PA selectivity, the cause of which is considered to be isolation of the vanadium centers. The antimony oxides used in the active material of the catalysts may comprise different antimony(III), antimony(IV) and/or antimony(V) compounds; usually, antimony trioxide or antimony pentoxide is used. EP 522871 describes the use of antimony pentoxide; US 2009/306409 and EP 1636161 disclose the use of antimony trioxide.

Compared to antimony tetroxide and antimony pentoxide, antimony trioxide has the property of spreading better on titanium dioxide, such that a significantly better distribution on the catalyst is achieved. Typically, the antimony trioxide used is single-phase senarmontite (cf. Schubert, U.-A. et al., Topics in Catalysis, 2001, vol. 15(2-4), pages 195 to 200). As well as cubic senarmontite, there is also an orthorhombic polymorph of antimony trioxide, called valentinite (Golunski, S. E. et al., Appl. Catal., 1989, vol. 48, pages 123 to 135).

Commercial catalyst systems for oxidation of o-xylene to phthalic anhydride typically consist of multiple catalyst zones arranged in succession in the reaction tube and filled with catalysts of different chemical composition. A typical configuration of the different zones is the combination of so-called "selective catalyst zones" in the first one or two zones at the reactor inlet side, which have high selectivity to Ca-value products at partial educt conversion, and "active catalyst zones" in the last one or two zones at the reactor outlet side, which have higher catalytic activity in order to ensure full conversion of educts and intermediate oxidation products to PA (Rosowski, F. et al., Catalysis today, 2010, vol. 157, pages 339 to 344; WO 2004014819). Catalyst systems with multiple catalyst zones are generally introduced into the reaction tube by consecutive infilling of the catalysts of the different zones through the top end of the upright reaction tube. Usually the reaction tube will not only be filled but also operated in an upright position, although the upright position of the reaction tube doesn't necessarily have to be maintained during operation. Depending on the sequence of the zones of the catalyst system in the reaction tube both ends of the reaction tube can in principle be used as inlet for the gas stream to be oxidized when the catalyst system has been filled in.

In US 2011/0124885 and US 2014/0213801 vanadium antimonate has been used to prepare the selective catalyst zones.

In PA catalyst systems antimony is generally known as promoter element that enhances selectivity while reducing catalyst activity. Therefore, in commercial PA catalyst systems only little or no antimony at all is usually present in the active catalyst zones, especially in the last zone.

U.S. Pat. No. 5,169,820 discloses silver-containing PA catalyst systems with two catalyst zones which both contain antimony trioxide. WO2006/125467 and WO2005/115615 disclose PA catalyst systems with three catalyst zones which contain 3.2 wt. % antimony trioxide in all catalyst zones and with a constant content not only of $Sb_2O_3$ but also $V_2O_5$ along the whole length of the catalyst system. WO2010/022830 discloses silver- and bismuth-containing PA catalyst systems with four or five catalyst zones which contain antimony trioxide in all catalyst zones and with 0.5 wt. % of $Sb_2O_3$ in the active material of the catalyst in the last catalyst zone towards the reactor outlet.

For the purpose of the present invention the following terms shall have the defined meaning:

Catalyst carrier (in German: Katalysatorträger) shall mean a macroscopic body in a usually flow-optimized form on which surface the catalytically active material is deposited in a coating process. The catalyst carrier is generally made from an inert or catalytically low active material.

Catalyst shell (in German: Katalysatorschicht) shall mean a comparatively thin layer of catalytically active material deposited on a catalyst carrier. Catalysts with more than one shell deposited on the same catalyst carrier are referred to as two-shell or multi-shell catalysts.

Coated catalyst (in German: Schalenkatalysator) shall mean a catalyst comprising one or more catalyst shells deposited on the surface of a catalyst carrier.

Catalyst zone (in German: Katalysatorlage) shall mean a macroscopic volume in a reactor filled with a catalyst of consistent chemical composition.

Catalyst system shall mean a sequential arrangement of two or more catalyst zones filled with catalysts of different chemical composition in a reactor.

For the purpose of the present invention the vanadium and antimony content of the active material of a catalyst is reported as vanadium pentoxide ($V_2O_5$) and antimony trioxide ($Sb_2O_3$), respectively. However, these values have been calculated from the analytically determined metal contents and do neither imply that vanadium and antimony are only present in the form of $V_2O_5$ and $Sb_2O_3$, respectively, nor that any $V_2O_5$ and $Sb_2O_3$ is present at all.

There is a constant need for catalysts for gas phase oxidations having a maximum conversion combined with high selectivity. In particular in PA synthesis, high PA yield with low concentration of side products such as phthalide and unconverted o-xylene among others is highly desirable. In the catalytic gas-phase oxidation of o-xylene or/and naphthalene for producing PA, the most important side reaction is the total oxidation of the educts and intermediates reducing the selectivity to the desired product.

It was an object of the present invention to develop a catalyst system for the oxidation of o-xylene and/or naphthalene to phthalic anhydride, which enables, at a low salt bath temperature, a high phthalic anhydride yield combined with a low o-xylene and phthalide content. A further object of the present invention was to develop and produce a catalyst system which can be operated at higher educt loadings and for extended operation periods and still satisfying the specifications with regard to the side product concentration limits.

This object is achieved by a catalyst system for oxidation of o-xylene and/or naphthalene to phthalic anhydride (PA) comprising at least four catalyst zones arranged in succession in the reaction tube and filled with catalysts of different chemical composition wherein the active materials of the catalysts comprise vanadium and titanium dioxide and the active material of the catalyst in the last catalyst zone at the reactor outlet contains antimony. In particular, the addition of a specific amount of antimony in a defined range to the last catalyst zone allows the increase of the selectivity to PA by the reduction of total oxidation processes in the active catalyst zones.

On embodiment of the present invention is therefore a catalyst system for oxidation of o-xylene and/or naphthalene to phthalic anhydride comprising at least four catalyst zones arranged in succession in the reaction tube and filled with catalysts of different chemical composition wherein the active materials of the catalysts comprise vanadium and titanium dioxide and the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt %, still more preferably between 1.1 and 1.7 wt. %, in particular between 1.2 and 1.6 wt. %.

BRIEF DESCRIPTION OF THE FIGURE

FIG. 1 shows the concentration of $CO_x$ ($CO+CO_2$) as a function of the Sb content (calculated as $Sb_2O_3$) in the last catalyst zone, Apparently there is an optimum Sb content at which total oxidation processes are kept to a minimum.

A preferred embodiment of the present invention is a catalyst system for oxidation of o-xylene and/or naphthalene to phthalic anhydride comprising at least four catalyst zones arranged in succession in the reaction tube and filled with catalysts of different chemical composition wherein the active materials of the catalysts in all catalyst zones comprise vanadium, titanium dioxide and antimony and the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt. %, still more preferably between 1.1 and 1.7 wt %, in particular between 1.2 and 1.6 wt,%.

Another preferred embodiment of the present invention is a catalyst system for oxidation of o-xylene and/or naphthalene to phthalic anhydride comprising at least four catalyst zones arranged in succession in the reaction tube and filled with catalysts of different chemical composition wherein the active materials of the catalysts in all catalyst zones comprise vanadium, titanium dioxide and antimony and the active materials of the catalysts in the last two catalyst zones towards the reactor outlet have a lower average antimony content than the active materials of the catalysts in the remaining catalyst zones towards the reactor inlet and the active material of the catalyst in the last catalyst zone towards the reactor outlet has an antimony content (calculated as antimony trioxide) between 0.7 to 3.0 wt. %, preferably between 0.9 and 2.5 wt %, more preferably between 1.0 and 1.80 wt. %, still more preferably between 1.1 and 1.7 wt. %, in particular between 1.2 and 1.6 wt. %.

Another preferred embodiment of the present invention is a catalyst system for oxidation of o-xylene and/or naphthalene to phthalic anhydride comprising at least four catalyst zones arranged in succession in the reaction tube and filled with catalysts of different chemical composition wherein the active materials of the catalysts in all catalyst zones comprise vanadium, titanium dioxide and antimony and the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt. %, still more preferably between 1.1 and 1.7 wt. %, in particular between 1.2 and 1.6 wt. % and a higher vanadium content than the catalysts in the selective catalyst zones.

In addition to the catalyst system according to the present invention the reaction tube may contain further zones which are filled with catalytically inactive or only poorly active material. Said further zones can be placed before or after the catalyst system (i.e. at the reactor inlet or outlet side) or even between the individual catalyst zones of the catalyst system according to the invention. For the purpose of the present invention the term "last catalyst zone towards the reactor outlet" refers to the catalyst zone of the catalyst system closest to the reactor outlet with a length of between 10 and 40% of the total length of the catalyst system and filled with material with regular catalytic activity.

Still another preferred embodiment of the present invention is a catalyst system for oxidation of o-xylene and/or naphthalene to phthalic anhydride comprising at least four catalyst zones arranged in succession in the reaction tube and filled with catalysts of different chemical composition wherein the active materials of the catalysts comprise vanadium and titanium dioxide and the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt. %, still more preferably between 1.1 and 1.7 wt. %, in particular between 1.2 and 1.6 wt. % and said last catalyst zone has a length of between 10 and 40% of the total length of the catalyst system.

PA catalysts are generally coated catalysts, in which the catalytically active material has been applied in the form of a shell to an inert catalyst carrier. The inert catalyst carrier used may be virtually all prior art catalyst carrier materials as used advantageously in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these carrier materials. The catalyst carrier can be used, for example, in the form of spheres, rings, tablets, spirals, tubes, extrudates or chippings. The dimensions of these catalyst carriers correspond to those of catalyst carriers used customarily for production of coated catalysts for the gas phase reactions of aromatic hydrocarbons. Preference is given to using steatite in the form of spheres having a diameter of 3 to 6 mm or of rings having an external diameter of 5 to 9 mm and a length of 3 to 8 mm and a wall thickness of 1 to 2 mm.

The catalyst systems according to the present invention comprise a catalytically active material which comprises, as well as antimony, at least also vanadium and titanium dioxide and can be applied to the catalyst carrier in one or more shells. Different shells may differ in their composition.

Another preferred embodiment of the present invention is a catalyst system as described above comprising catalytically active material which comprises antimony, vanadium and titanium dioxide, but no silver and/or bismuth.

Another embodiment of the present invention is therefore a process for production of a catalyst system for oxidation of o-xylene and/or naphthalene to phthalic anhydride with at least four catalyst zones arranged in succession in the reaction tube and filled with catalysts of different chemical composition, comprising the step of applying a catalytically active material comprising antimony, vanadium and titanium dioxide to a catalyst carrier in one or more shells, wherein the active materials of the catalysts comprise vanadium and titanium dioxide and the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt. %, still more preferably between 1.1 and 1.7 wt. %, in particular between 1.2 and 1.6 wt. %.

The catalytically active material, based on the total amount of the catalytically active material, usually comprises 1% to 40% by weight of vanadium (calculated as vanadium oxide $V_2O_5$) and 60% to 99% by weight of titanium dioxide $TiO_2$. In preferred embodiments, the catalytically active material may additionally comprise up to 1% by weight of a cesium compound, calculated as Cs, up to 1% by weight of a phosphorus compound, calculated as P, and up to 10% by weight of antimony compounds, calculated as $Sb_2O_3$. All FIGURES for the composition of the catalytically active material are based on the calcined state thereof, for example after calcination of the catalyst at 450° C. for one hour.

Typically, titanium dioxide in the anatase modification is used for catalytically active material. The titanium dioxide preferably has a BET surface area of 15 to 60 $m^2/g$, especially 15 to 45 $m^2/g$, more preferably 13 to 28 $m^2/g$. The titanium dioxide used may consist of a single titanium dioxide or a mixture of titanium dioxides. In the latter case, the value for the BET surface area is determined as the weighted mean of the contributions of the individual titanium dioxides. The titanium dioxide used consists, for example, advantageously of a mixture of a $TiO_2$ having a BET surface area of 5 to 15 $m^2/g$ and a $TiO_2$ having a BET surface area of 15 to 50 $m^2/g$. In a preferred embodiment of the present invention the titanium dioxide in the active material of the last two catalyst zones towards the reactor outlet has a higher average BET surface area than in the other catalyst zones.

Suitable vanadium sources are particularly vanadium pentoxide or ammonium metavanadate. Suitable antimony sources are various antimony trioxides, and various vanadium antimonates can be used as well. Useful phosphorus sources include especially phosphoric acid, phosphorous acid, hypophosphorous acid, ammonium phosphate or phosphoric esters, and in particular ammonium dihydrogenphosphate. Useful sources of cesium include the oxide or hydroxide or the salts which can be converted thermally to the oxide, such as carboxylates, especially the acetate, malonate or oxalate, carbonate, hydrogencarbonate, sulfate or nitrate.

As well as the optional additions of cesium and phosphorus, small amounts of a multitude of other oxidic compounds which influence the activity and selectivity of the catalyst as promoters, for example by lowering or increasing the activity thereof, may be present in the catalytically active material. Examples of such promoters include the alkali metals, more particularly (in addition to cesium, which has already been mentioned) also lithium, potassium and rubidium, which are usually used in the form of their oxides or hydroxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony tetroxide, antimony pentoxide and cerium oxide.

In addition, among the promoters mentioned, useful additives preferably also include the oxides of niobium and tungsten in amounts of 0.01% to 0.50% by weight, based on the catalytically active material.

The shell(s) of the coated catalyst are appropriately applied by spray application of a suspension of $TiO_2$ and $V_2O_5$, which optionally comprises sources of the abovementioned promoter elements, to the fluidized carrier. Before the coating, the suspension is preferably stirred for a sufficiently long period, for example 2 to 30 hours, especially 12 to 25 hours, to break up agglomerates of the suspended solids and to obtain a homogeneous suspension. The suspension typically has a solids content of 20% to 50% by weight. The suspension medium is generally aqueous, for example water itself or an aqueous mixture with a water-miscible organic solvent such as methanol, ethanol, isopropanol, formamide and the like.

In general, organic binders are added to the suspension, preferably copolymers, advantageously in the form of an aqueous dispersion, of acrylic acid/maleic acid, vinyl acetate/vinyl laurate, vinyl acetate/acrylate, styrene/acrylate and vinyl acetate/ethylene. The binders are commercially available as aqueous dispersions having a solids content of, for example, 35% to 65% by weight. The amount of such binder dispersions used is generally 2% to 45% by weight, preferably 5% to 35% by weight, more preferably 7% to 20% by weight, based on the weight of the suspension.

The carrier is fluidized in, for example, a fluidized bed apparatus in an ascending gas stream, especially air. The apparatuses usually consist of a conical or spherical vessel in which the fluidizing gas is introduced from the bottom or from the top through an immersed tube. The suspension is sprayed into the fluidized bed via nozzles from the top, at the side or from below. It is advantageous to use a riser tube arranged centrally or concentrically around the immersed tube. Within the riser tube, there is a higher gas velocity which transports the carrier particles upward. Within the outer ring, the gas velocity is only slightly above the fluidization velocity. Thus, the particles are moved vertically in a circular manner. A suitable fluidized bed apparatus is described, for example, in DE-A 4006935.

In the coating of the catalyst carrier with the catalytically active material, coating temperatures of 20 to 500° C. are generally employed, and the coating can be done under atmospheric pressure or under reduced pressure. In general, the coating is done at 0° C. to 200° C., preferably at 20 to 150° C., especially at 60 to 120° C.

The shell thickness of the catalytically active material is generally 0.02 to 0.2 mm, preferably 0.05 to 0.15 mm. The average active material content in the catalysts of the whole catalyst system is typically between 2% and 25% by weight, preferably between 5% and 20% by weight.

As a result of thermal treatment of the pre-catalyst thus obtained at temperatures above 200 to 500° C., the binder escapes from the shell applied through thermal decomposition and/or combustion. Preference is given to effecting the thermal treatment in situ in the gas phase oxidation reactor.

Another embodiment of the present invention is the use of a catalyst system as described above for the gas phase oxidation of hydrocarbons. Another preferred embodiment of the present invention is the use of a catalyst system as described above for the gas phase oxidation of o-xylene and/or naphthalene to phthalic anhydride.

The invention further provides a process for gas phase oxidation in which a gas stream comprising at least one hydrocarbon and molecular oxygen is passed through a catalyst system comprising at least four catalyst zones arranged in succession in the reaction tube and filled with catalysts of different chemical composition wherein the active material of the catalysts comprise vanadium and titanium dioxide and the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt. %, still more preferably between 1.1 and 1.7 wt. %, in particular between 1.2 and 1.6 wt. %.

A preferred embodiment of the present invention is a process for gas phase oxidation in which a gas stream comprising at least one hydrocarbon and molecular oxygen is passed through a catalyst system comprising at least four catalyst zones arranged in succession in the reaction tube wherein the active material of the catalyst in the last catalyst zone towards the reactor outlet has an antimony content (calculated as antimony trioxide) between 0.7 to 3.0 wt. %, preferably between 0.9 and 2.5 wt. %, more preferably between 1.0 and 1.8 wt. %, still more preferably between 1.1 and 1.7 wt. %, in particular between 1.2 and 1.6 wt. % and said last catalyst zone has a length of between 10 and 40% of the total length of the catalyst system.

Another embodiment of the present invention is a process for gas phase oxidation as outlined above wherein o-xylene and/or naphthalene are oxidized to phthalic anhydride.

EXAMPLES

Production of Five-Zone Catalyst System

Catalyst Zone CZ1:
Preparation of the Vanadium Antimonate:

A thermostated jacketed glass vessel was initially charged with 5 L of demineralized water and 1566.1 g of antimony trioxide, which consisted of 99% by weight of senarmontite and 1% by weight of valentinite, were suspended therein by stirring at 90° C. for 18 hours. Then 2446.9 g of vanadium pentoxide and a further liter of demineralized water were added and the mixture was stirred at 90° C. for 25 hours. Thereafter, the suspension was cooled to 80° C. and dried by spray drying. The inlet temperature was 340° C., the outlet temperature 120° C. The spray powder thus obtained had a vanadium content of 32% by weight and an antimony content of 30% by weight.

Preparation of the Suspension and Coating:

3.87 g of cesium carbonate, 349.69 g of titanium dioxide (Fuji TA 100CT, anatase, BET surface area 28 $m^2/g$), 188.29 g of titanium dioxide (Fuji TA 100, anatase, BET surface area 8 $m^2/g$), and 75.43 g of vanadium antimonate (synthesized as described above) were suspended in 1583 g of demineralized water and stirred for 18 hours, in order to obtain a homogeneous distribution. To this suspension were added 85 g of organic binder, consisting of a copolymer of vinyl acetate and vinyl laurate in the form of a 50% by weight aqueous dispersion. In a fluidized bed apparatus, 750 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.3% by weight. The analyzed composition of the active material consisted of 7.1% by weight of V (calculated as $V_2O_5$), 4.5% by weight of Sb (calculated as $Sb_2O_3$), 0.50% by weight of Cs, remainder $TiO_2$.

Catalyst Zone CZ2:

2.86 g of cesium carbonate, 427.54 g of titanium dioxide (Fuji TA 100C, anatase, BET surface area 20 $m^2/g$), 127.71 g of titanium dioxide (Fuji TA 100, anatase, BET surface area 8 $m^2/g$), 43.47 g of vanadium pentoxide and 11.13 g of antimony trioxide (77% by weight of senarmontite and 23% by weight of valentinite) were suspended in 1588 g of demineralized water and stirred for 18 hours, in order to obtain a homogeneous distribution. To this suspension were added 103 g of organic binder, consisting of a copolymer of vinyl acetate and vinyl laurate in the form of a 50% by weight aqueous dispersion. In a fluidized bed apparatus, 910 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 10% by weight. The analyzed composition of the active material consisted of 7.1% by weight of V (calculated as $V_2O_5$), 1.8% by weight of Sb (calculated as $Sb_2O_3$), 0.38% by weight of Cs, remainder $TiO_2$.

Catalyst Zone CZ3:

2.40 g of cesium carbonate, 468.67 g of titanium dioxide (Fuji TA 100C, anatase, BET surface area 20 $m^2/g$), 76.29 g of titanium dioxide (Fuji TA 100, anatase, BET surface area 8 $m^2/g$), 48.67 g of vanadium pentoxide and 16.69 g of antimony trioxide (77% by weight of senarmontite and 23% by weight of valentinite) were suspended in 1588 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 770 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.95% by weight of V (calculated as $V_2O_5$), 2.7% by weight of Sb (calculated as $Sb_2O_3$), 0.31% by weight of Cs, remainder $TiO_2$.

Catalyst Zone CZ4:

1.65 g of cesium carbonate, 370.08 g of titanium dioxide (Fuji TA 100CT, anatase, BET surface area 28 $m^2/g$), 158.60 g of titanium dioxide (Fuji TA 100, anatase, BET surface area 8 $m^2/g$), 67.34 g of vanadium pentoxide and 14.84 g of antimony trioxide (77% by weight of senarmontite and 23% by weight of valentinite) were suspended in 1588 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 775 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 11.0% by weight of V (calculated as $V_2O_5$), 2.4% by weight of Sb (calculated as $Sb_2O_3$), 0.2% by weight of Cs, remainder $TiO_2$.

Catalyst Zone CZ5:

8.63 g of ammonium hydrogenphosphate, 435.8 g of titanium dioxide (Fuji TA 100CT, anatase, BET surface area 28 $m^2/g$), 48.42 g of titanium dioxide (Fuji TA 100, anatase, BET surface area 8 $m^2/g$), 122.44 g of vanadium pentoxide and 3.09 g of antimony trioxide (66% by weight of senarmontite and 34% by weight of valentinite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of V (calculated as $V_2O_5$), 0.38% by weight of P, 0.5% by weight of Sb (calculated as $Sb_2O_3$), remainder $TiO_2$.

Catalyst Zone CZ6:

8.63 g of ammonium hydrogenphosphate, 434.71 g of titanium dioxide (Fuji TA 100CT, anatase, BET surface area 28 $m^2/g$), 48.24 g of titanium dioxide (Fuji TA 100, anatase, BET surface area 8 $m^2/g$), 122.44 g of vanadium pentoxide and 4.95 g of antimony trioxide (66% by weight of senarmontite and 34% by weight of valentinite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of V (calculated as $V_2O_5$), 0.38% by weight of P, 0.8% by weight of Sb (calculated as $Sb_2O_3$), remainder $TiO_2$.

Catalyst Zone CZ7:

8.63 g of ammonium hydrogenphosphate, 431.97 g of titanium dioxide (Fuji TA 100CT, anatase, BET surface area 28 $m^2/g$), 48.00 g of titanium dioxide (Fuji TA 100, anatase, BET surface area 8 $m^2/g$), 122.44 g of vanadium pentoxide and 8.04 g of antimony trioxide (66% by weight of senarmontite and 34% by weight of valentinite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of V (calculated as $V_2O_5$), 0.38% by weight of P, 1.3% by weight of Sb (calculated as $Sb_2O_3$), remainder $TiO_2$.

Catalyst Zone CZ8:

8.63 g of ammonium hydrogenphosphate, 427.56 g of titanium dioxide (Fuji TA 100CT, anatase, BET surface area 28 $m^2/g$), 47.51 g of titanium dioxide (Fuji TA 100, anatase, BET surface area 8 $m^2/g$), 122.44 g of vanadium pentoxide and 12.24 g of antimony trioxide (66% by weight of senarmontite and 34% by weight of valentinite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of V (calculated as $V_2O_5$), 0.38% by weight of P, 2.0% by weight of Sb (calculated as $Sb_2O_3$), remainder $TiO_2$.

Catalyst Zone CZ9:

7.96 g of ammonium hydrogenphosphate, 387.05 g of titanium dioxide (Fuji TA 100CT, anatase, BET surface area 28 $m^2/g$), 96.76 g of titanium dioxide (Fuji TA 100, anatase, BET surface area 8 m$^2$/g) and 126.12 g of vanadium pentoxide were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of V (calculated as V$_2$O$_5$), 0.38% by weight of P, remainder TiO$_2$.

Catalyst Zone CZ10:

8.63 g of ammonium hydrogenphosphate, 430.31 g of titanium dioxide (Fuji TA 100CT, anatase, BET surface area 28 m$^2$/g), 47.81 g of titanium dioxide (Fuji TA 100, anatase, BET surface area 8 m$^2$/g), 122.44 g of vanadium pentoxide and 9.27 g of antimony trioxide (100% by weight of senarmontite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 10.0% by weight. The analyzed composition of the active material consisted of 20% by weight of V (calculated as V$_2$O$_5$), 0.38% by weight of P, 1.5% by weight of Sb (calculated as Sb$_2$O$_3$), remainder TiO$_2$.

Catalyst Zone CZ11:

8.63 g of ammonium hydrogenphosphate, 430.37 g of titanium dioxide (Fuji TA 100CT, anatase, BET surface area 28 m$^2$/g), 53.37 g of titanium dioxide (Fuji TA 100, anatase, BET surface area 8 m$^2$/g), 67.34 g of vanadium pentoxide and 9.27 g of antimony trioxide (100% by weight of senarmontite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 12.0% by weight. The analyzed composition of the active material consisted of 11% by weight of V (calculated as V$_2$O$_5$), 0.38% by weight of P, 1.5% by weight of Sb (calculated as Sb$_2$O$_3$), remainder TiO$_2$.

Examples with a Five-Zone Catalyst System

Example 1a to 1e

The catalytic oxidation of o-xylene to phthalic anhydride was conducted in a salt bath-cooled tubular reactor having an internal tube diameter of 25 mm and a length of 350 cm. From reactor inlet to reactor outlet, 80 cm of CZ1, 60 cm of CZ2, 70 cm of CZ3, 50 cm of CZ4 and 60 cm of CZ5 (Example 1a, comparative) or CZ6 (Example 1 b) or CZ7 (Example 1c) or CZ8 (Example 1d) or CZ9 (Example 1e, comparative) were introduced. For temperature regulation, the tubular reactor was surrounded by a salt melt; a thermowell of external diameter 4 mm with an installed thermocouple served for catalyst temperature measurement. An air flow of 4.0 Nm$^3$(STP)/h with loadings of 99 to 99.4% by weight o-xylene of 30 to 100 g$_{o-xylene}$/Nm$^3$(STP)$_{air}$ was passed through the tubular reactor.

FIG. 1 shows the concentration of CO$_x$ (CO+CO$_2$) as a function of the Sb content (calculated as Sb$_2$O$_3$) in the last catalyst zone. Apparently there is an optimum Sb content at which total oxidation processes are kept to a minimum.

FIG. 1: Comparison of CO$_x$ concentration in the reactor out gas as function of the Sb content in the last catalyst zone at a salt bath temperature of 364° C., o-xylene loading of 69 g$_{o-x}$/Nm$^3$, and a total air flow rate of 4 Nm$^3$(STP)/h.

Example 2

The catalytic oxidation of o-xylene to phthalic anhydride was conducted in a salt bath-cooled tubular reactor having an internal tube diameter of 25 mm and a length of 350 cm. From reactor inlet to reactor outlet, 70 cm of CZ1, 50 cm of CZ2, 60 cm of CZ3, 50 cm of CZ4 and 90 cm of CZ10 were introduced. For temperature regulation, the tubular reactor was surrounded by a salt melt; a thermowell of external diameter 4 mm with an installed thermocouple served for catalyst temperature measurement. An air flow of 4.0 Nm$^3$(STP)/h with loadings of 99 to 99.4% by weight o-xylene of 30 to 100 g$_{o-xylene}$/Nm$^3$(STP)$_{air}$ was passed through the tubular reactor.

TABLE 1

Catalyst composition of five-layer catalyst system of example 2.

| | | Catalyst zone | | | | |
|---|---|---|---|---|---|---|
| | | CZ1 | CZ2 | CZ3 | CZ4 | CZ10 |
| Active material | % | 8.30 | 10.0 | 8.50 | 8.50 | 10.00 |
| V$_2$O$_5$ | % | 7.10 | 7.10 | 7.95 | 11.00 | 20.00 |
| Sb$_2$O$_3$ | % | 4.50 | 1.80 | 2.70 | 2.40 | 1.50 |
| Cs | % | 0.50 | 0.38 | 0.31 | 0.22 | 0 |
| P | % | 0 | 0 | 0 | 0 | 0.38 |
| TiO$_2$ | % | 87.90 | 90.72 | 89.04 | 86.38 | 78.12 |
| BET-Surface area | m$^2$/g | 20 | 17 | 18 | 21 | 26 |
| Zone length | cm | 70 | 50 | 60 | 50 | 90 |

TABLE 2

Catalytic performance of the example 2 catalyst system at a total air flow rate of 4 Nm$^3$(STP)/h.

| Loading [g$_{o-x}$/m$^3$ (STP)$_{air}$] | Salt bath temperature [° C.] | $Y_{PA}$[a] [% by wt.] | $Y_{o-x}$[b] [% by wt.] | $Y_{PHD}$[c] [% by wt.] |
|---|---|---|---|---|
| 61.0 | 370.0 | 113.8 | 0.00 | 0.07 |
| 79.0 | 362.0 | 115.1 | 0.00 | 0.07 |
| 90.0 | 356.0 | 115.0 | 0.01 | 0.06 |
| 100.0 | 353.5 | 115.0 | 0.02 | 0.07 |

[a] PA yield
[b] o-xylene yield
[c] phthalide yield

Example 3

The catalytic oxidation of o-xylene to phthalic anhydride was conducted in a salt bath-cooled tubular reactor having an internal tube diameter of 25 mm and a length of 350 cm. From reactor inlet to reactor outlet, 70 cm of CZ1, 50 cm of CZ2, 60 cm of CZ3, 50 cm of CZ4 and 90 cm of CZ7 were introduced. For temperature regulation, the tubular reactor was surrounded by a salt melt; a thermowell of external diameter 4 mm with an installed thermocouple served for catalyst temperature measurement. An air flow of 4.0 Nm³ (STP)/h with loadings of 99 to 99.4% by weight o-xylene of 30 to 100 $g_{o\text{-}xylene}/Nm^3(STP)_{air}$ was passed through the tubular reactor.

TABLE 3

Catalyst composition of five-layer catalyst system of example 3.

|  |  | Catalyst zone | | | | |
| --- | --- | --- | --- | --- | --- | --- |
|  |  | CZ1 | CZ2 | CZ3 | CZ4 | CZ7 |
| Active material | % | 8.30 | 10.0 | 8.50 | 8.50 | 9.10 |
| V₂O₅ | % | 7.10 | 7.10 | 7.95 | 11.00 | 20.00 |
| Sb₂O₃ | % | 4.50 | 1.80 | 2.70 | 2.40 | 1.30 |
| Cs | % | 0.50 | 0.38 | 0.31 | 0.22 | 0 |
| P | % | 0 | 0 | 0 | 0 | 0.38 |
| TiO₂ | % | 87.90 | 90.72 | 89.04 | 86.38 | 78.12 |
| BET-Surface area | m²/g | 20 | 17 | 18 | 21 | 26 |
| Zone length | cm | 70 | 50 | 60 | 50 | 90 |

TABLE 4

Catalytic performance of the example 3 catalyst system at a total air flow rate of 4 Nm³(STP)/h.

| Loading [$g_{o\text{-}X}/m^3\,(STP)_{air}$] | Salt bath temperature [° C.] | $Y_{PA}{}^a$ [% by wt.] | $Y_{o\text{-}X}{}^b$ [% by wt.] | $Y_{PHD}{}^c$ [% by wt.] |
| --- | --- | --- | --- | --- |
| 66.0 | 366.0 | 113.1 | 0.03 | 0.15 |
| 85.0 | 360.6 | 114.0 | 0.04 | 0.12 |
| 90.0 | 348.5 | 115.3 | 0.06 | 0.08 |

$^a$ PA yield
$^b$ o-xylene yield
$^c$ phthalide yield

Example 4

The catalytic oxidation of o-xylene to phthalic anhydride was conducted in a salt bath-cooled tubular reactor having an internal tube diameter of 25 mm and a length of 350 cm. From reactor inlet to reactor outlet, 70 cm of CZ1, 50 cm of CZ2, 60 cm of CZ3, 50 cm of CZ4 and 90 cm of CZ11 were introduced. For temperature regulation, the tubular reactor was surrounded by a salt melt; a thermowell of external diameter 4 mm with an installed thermocouple served for catalyst temperature measurement. An air flow of 4.0 Nm³ (STP)/h with loadings of 99 to 99.4% by weight o-xylene of 30 to 100 $g_{o\text{-}xylene}/Nm^3(STP)_{air}$ was passed through the tubular reactor.

TABLE 5

Catalyst composition of five-layer catalyst system of example 4.

|  |  | Catalyst zone | | | | |
| --- | --- | --- | --- | --- | --- | --- |
|  |  | CZ1 | CZ2 | CZ3 | CZ4 | CZ11 |
| Active material | % | 8.30 | 10.0 | 8.50 | 8.50 | 12.00 |
| V₂O₅ | % | 7.10 | 7.10 | 7.95 | 11.00 | 11.00 |
| Sb₂O₃ | % | 4.50 | 1.80 | 2.70 | 2.40 | 1.50 |
| Cs | % | 0.50 | 0.38 | 0.31 | 0.22 | 0 |
| P | % | 0 | 0 | 0 | 0 | 0.38 |
| TiO₂ | % | 87.90 | 90.72 | 89.04 | 86.38 | 87.12 |
| BET-Surface area | m²/g | 20 | 17 | 18 | 21 | 26 |
| Zone length | cm | 70 | 50 | 60 | 50 | 90 |

TABLE 6

Catalytic performance of the example 4 catalyst system at a total air flow rate of 4 Nm³(STP)/h.

| Loading [$g_{o\text{-}X}/m^3\,(STP)_{air}$] | Salt bath temperature [° C.] | $Y_{PA}{}^a$ [% by wt.] | $Y_{o\text{-}X}{}^b$ [% by wt.] | $Y_{PHD}{}^c$ [% by wt.] |
| --- | --- | --- | --- | --- |
| 65.0 | 370.0 | 112.5 | 0.01 | 0.08 |
| 79.0 | 360.0 | 113.9 | 0.01 | 0.09 |
| 88.0 | 357.0 | 114.7 | 0.02 | 0.08 |
| 98.0 | 352.0 | 114.2 | 0.02 | 0.06 |

$^a$ PA yield
$^b$ o-xylene yield
$^c$ phthalide yield

Example 5

(Comparative)

The catalytic oxidation of o-xylene to phthalic anhydride was conducted in a salt bath-cooled tubular reactor having an internal tube diameter of 25 mm and a length of 350 cm. From reactor inlet to reactor outlet, 80 cm of CZ1, 60 cm of CZ2, 70 cm of CZ3, 50 cm of CZ4 and 60 cm of CZ9 were introduced. For temperature regulation, the tubular reactor was surrounded by a salt melt; a thermowell of external diameter 4 mm with an installed thermocouple served for catalyst temperature measurement. An air flow of 4.0 Nm³ (STP)/h with loadings of 99 to 99.4% by weight o-xylene of 30 to 100 $g_{o\text{-}xylene}/Nm^3(STP)_{air}$ was passed through the tubular reactor.

TABLE 7

Catalyst composition of five-layer catalyst system of example 5.

|  |  | Catalyst zone | | | | |
| --- | --- | --- | --- | --- | --- | --- |
|  |  | CZ1 | CZ2 | CZ3 | CZ4 | CZ9 |
| Active material | % | 8.30 | 10.0 | 8.50 | 8.50 | 9.10 |
| V₂O₅ | % | 7.10 | 7.10 | 7.95 | 11.00 | 20.00 |
| Sb₂O₃ | % | 4.50 | 1.80 | 2.70 | 2.40 | 0 |
| Cs | % | 0.50 | 0.38 | 0.31 | 0.22 | 0 |
| P | % | 0 | 0 | 0 | 0 | 0.38 |
| TiO₂ | % | 87.90 | 90.72 | 89.04 | 86.38 | 79.62 |
| BET-Surface area | m²/g | 20 | 17 | 18 | 21 | 23 |
| Zone length | cm | 80 | 60 | 70 | 50 | 60 |

TABLE 8

Catalytic performance of the example 5 catalyst system (comparative) at a total air flow rate of 4 Nm³(STP)/h.

| Loading [$g_{o-X}$/m³ (STP)$_{air}$] | Salt bath temperature [° C.] | $Y_{PA}$ [a] [% by wt,] | $Y_{o-X}$ [b] [% by wt,] | $Y_{PHD}$ [c] [% by wt,] |
|---|---|---|---|---|
| 66.0 | 364.0 | 111.5 | 0.02 | 0.05 |
| 78.0 | 359.5 | 112.3 | 0.02 | 0.06 |
| 95.0 | 354.5 | 112.1 | 0.04 | 0.08 |
| 100.0 | 350.5 | 113.5 | 0.09 | 0.12 |

[a] PA yield
[b] o-xylene yield
[c] phthalide yield

Production of a Four-Zone Catalyst System

Catalyst Zone CZ12:

2.86 g of cesium carbonate, 427.54 g of titanium dioxide (Fuji TA 100C, anatase, BET surface area 20 m²/g), 127.71 g of titanium dioxide (Fuji TA 100, anatase, BET surface area 8 m²/g), 43.47 g of vanadium pentoxide and 11.13 g of antimony trioxide (77% by weight of senarmontite and 23% by weight of valentinite) were suspended in 1588 g of demineralized water and stirred for 18 hours, in order to obtain a homogeneous distribution. To this suspension were added 103 g of organic binder, consisting of a copolymer of vinyl acetate and vinyl laurate in the form of a 50% by weight aqueous dispersion. In a fluidized bed apparatus, 910 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 10% by weight. The analyzed composition of the active material consisted of 7.1% by weight of V (calculated as $V_2O_5$), 1.8% by weight of Sb (calculated as $Sb_2O_3$), 0.38% by weight of Cs, remainder $TiO_2$.

Catalyst Zone CZ13:

2.40 g of cesium carbonate, 468.67 g of titanium dioxide (Fuji TA 100C, anatase, BET surface area 20 m²/g), 76.29 g of titanium dioxide (Fuji TA 100, anatase, BET surface area 8 m²/g), 48.67 g of vanadium pentoxide and 16.69 g of antimony trioxide (77% by weight of senarmontite and 23% by weight of valentinite) were suspended in 1588 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 770 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.95% by weight of V (calculated as $V_2O_5$), 2.7% by weight of Sb (calculated as $Sb_2O_3$), 0.31% by weight of Cs, remainder $TiO_2$.

Catalyst Zone CZ14:

1.65 g of cesium carbonate, 370.08 g of titanium dioxide (Fuji TA 100CT, anatase, BET surface area 28 m²/g), 158.60 g of titanium dioxide (Fuji TA 100, anatase, BET surface area 8 m²/g), 67.34 g of vanadium pentoxide and 14.84 g of antimony trioxide (77% by weight of senarmontite and 23% by weight of valentinite) were suspended in 1588 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 775 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 11.0% by weight of V (calculated as $V_2O_5$), 2.4% by weight of Sb (calculated as $Sb_2O_3$), 0.2% by weight of Cs, remainder $TiO_2$.

Catalyst Zone CZ15:

8.63 g of ammonium hydrogenphosphate, 430.31 g of titanium dioxide (Fuji TA 100CT, anatase, BET surface area 28 m²/g), 47.81 g of titanium dioxide (Fuji TA 100, anatase, BET surface area 8 m²/g), 122.44 g of vanadium pentoxide and 9.27 g of antimony trioxide (100% by weight of senarmontite) were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 10.0% by weight. The analyzed composition of the active material consisted of 20% by weight of V (calculated as $V_2O_5$), 0.38% by weight of P, 1.5% by weight of Sb (calculated as $Sb_2O_3$), remainder $TiO_2$.

Catalyst Zone CZ16:

7.96 g of ammonium hydrogenphosphate, 387.05 g of titanium dioxide (Fuji TA 100CT, anatase, BET surface area 28 m²/g), 96.76 g of titanium dioxide (Fuji TA 100, anatase, BET surface area 8 m²/g) and 126.12 g of vanadium pentoxide were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of V (calculated as $V_2O_5$), 0.38% by weight of P, remainder $TiO_2$.

Examples with a Four-Zone Catalyst System

Example 6

The catalytic oxidation of o-xylene to phthalic anhydride was conducted in a salt bath-cooled tubular reactor having an internal tube diameter of 25 mm and a length of 350 cm. From reactor inlet to reactor outlet, 90 cm of CZ12, 70 cm of CZ13, 70 cm of CZ14 and 90 cm of CZ15 were introduced. For temperature regulation, the tubular reactor was surrounded by a salt melt; a thermowell of external diameter 4 mm with an installed thermocouple served for catalyst temperature measurement. An air flow of 4.0 Nm³(STP)/h with loadings of 99 to 99.4% by weight o-xylene of 30 to 100 $g_{o-xylene}$/Nm³(STP)$_{air}$ was passed through the tubular reactor.

TABLE 9

Catalyst composition of four-layer catalyst system of example 6.

| Catalyst zone |  | CZ12 | CZ13 | CZ14 | CZ15 |
|---|---|---|---|---|---|
| Active material | % | 9.10 | 8.50 | 8.50 | 10.00 |
| $V_2O_5$ | % | 7.10 | 7.95 | 11.00 | 20.00 |
| $Sb_2O_3$ | % | 1.80 | 2.70 | 2.40 | 1.50 |
| Cs | % | 0.38 | 0.31 | 0.22 | 0 |
| P | % | 0 | 0 | 0 | 0.38 |
| $TiO_2$ | % | 90.72 | 89.04 | 86.38 | 78.12 |
| BET-Surface area | m$^2$/g | 16 | 18 | 21 | 26 |
| Zone lenght | cm | 90 | 70 | 70 | 90 |

TABLE 10

Catalytic performance of the example 6 catalyst system at a total air flow rate of 4 Nm$^3$(STP)/h.

| Loading [g$_{o-X}$/m$^3$ (STP)$_{air}$] | Salt bath temperature [° C.] | $Y_{PA}$$^a$ [% by wt,] | $Y_{o-X}$$^b$ [% by wt,] | $Y_{PHD}$$^c$ [% by wt,] |
|---|---|---|---|---|
| 68.0 | 363.0 | 113.4 | 0.00 | 0.06 |
| 77.0 | 358.0 | 114.0 | 0.01 | 0.06 |
| 80.0 | 355.0 | 114.7 | 0.01 | 0.05 |

$^a$ PA yield
$^b$ o-xylene yield
$^c$ phthalide yield

Example 7

(Comparative)

The catalytic oxidation of o-xylene to phthalic anhydride was conducted in a salt bath-cooled tubular reactor having an internal tube diameter of 25 mm and a length of 350 cm. From reactor inlet to reactor outlet, 130 cm of CZ12, 70 cm of CZ13, 50 cm of CZ14 and 60 cm of CZ16 were introduced. For temperature regulation, the tubular reactor was surrounded by a salt melt; a thermowell of external diameter 4 mm with an installed thermocouple served for catalyst temperature measurement. An air flow of 4.0 Nm$^3$(STP)/h with loadings of 99 to 99.4% by weight o-xylene of 30 to 100 g$_{o-xylene}$/Nm$^3$(STP)$_{air}$ was passed through the tubular reactor.

TABLE 11

Catalyst composition of four-layer catalyst system of example 7.

| Catalyst zone |  | CZ12 | CZ13 | CZ14 | CZ16 |
|---|---|---|---|---|---|
| Active material | % | 9.10 | 8.50 | 8.50 | 9.10 |
| $V_2O_5$ | % | 7.10 | 7.95 | 11.00 | 20.00 |
| $Sb_2O_3$ | % | 1.80 | 2.70 | 2.40 | 0 |
| Cs | % | 0.38 | 0.31 | 0.22 | 0 |
| P | % | 0 | 0 | 0 | 0.38 |
| $TiO_2$ | % | 90.72 | 89.04 | 86.38 | 79.62 |
| BET-Surface area | m$^2$/g | 16 | 18 | 21 | 23 |
| Zone lenght | cm | 130 | 70 | 50 | 60 |

TABLE 12

Catalytic performance of the example 7 catalyst system (comparative) at a total air flow rate of 4 Nm$^3$(STP)/h.

| Loading [g$_{o-X}$/m$^3$ (STP)$_{air}$] | Salt bath temperature [° C.] | $Y_{PA}$$^a$ [% by wt,] | $Y_{o-X}$$^b$ [% by wt,] | $Y_{PHD}$$^c$ [% by wt,] |
|---|---|---|---|---|
| 60.0 | 363.0 | 110.9 | 0.02 | 0.06 |
| 74.0 | 358.0 | 112.3 | 0.04 | 0.08 |
| 80.0 | 354.0 | 113.0 | 0.07 | 0.12 |

$^a$ PA yield
$^b$ o-xylene yield
$^c$ phthalide yield

The invention claimed is:

1. A catalyst system for oxidation of o-xylene and/or naphthalene to phthalic anhydride comprising at least four catalyst zones arranged in succession in a reaction tube and filled with catalysts of different chemical composition wherein the catalytically active material of the catalyst is applied to an inert catalyst carrier and comprises antimony, vanadium and titanium dioxide and the active material of the catalyst in the last catalyst zone towards the reactor outlet has an antimony content (calculated as antimony trioxide) between 0.9 to 1.8 wt. %.

2. The catalyst system according to claim 1, wherein the active materials of the catalysts in the last two catalyst zones towards the reactor outlet have a lower average antimony content than the active materials of the catalysts in the remaining catalyst zones towards the reactor inlet.

3. The catalyst system according to claim 1, wherein the active material of the catalysts in the last two catalyst zones towards the reactor outlet have a higher vanadium content than in the other catalyst zones.

4. The catalyst system according to claim 1, wherein the last catalyst zone has a length of between 10 and 40% of the total length of the catalyst system.

5. The catalyst system according to claim 1, wherein the active material does not comprise silver and/or bismuth.

6. The catalyst system according to claim 1, wherein the active material comprises 1% to 40% by weight of vanadium (calculated as vanadium oxide $V_2O_5$) and 60% to 99% by weight of titanium dioxide $TiO_2$.

7. The catalyst system according to claim 1, wherein the average active material content in the catalysts of the whole catalyst system is between 2% and 25% by weight based on the whole catalyst system.

8. A process for production of the catalyst system according to claim 1, comprising the step of applying the catalytically active material comprising antimony, vanadium and titanium dioxide to a catalyst carrier in one or more shells, wherein the active material of the catalyst in the last catalyst zone towards the reactor outlet has an antimony content (calculated as antimony trioxide) between 0.9 to 1.8 wt. %.

9. A process for gas phase oxidation in which a gas stream comprising at least one hydrocarbon and molecular oxygen is passed through a catalyst system according to claim 1.

10. The process according to claim 9, wherein o-xylene and/or naphthalene are oxidized to phthalic anhydride.

11. The catalyst system according to claim 4, wherein the active material of the catalyst in the last catalyst zone towards the reactor outlet has an antimony content (calculated as antimony trioxide) between 1.0 to 1.8 wt. %.

12. The catalyst system according to claim 6, wherein the active material of the catalyst in the last catalyst zone towards the reactor outlet has an antimony content (calculated as antimony trioxide) between 1.1 to 1.7 wt. %.

13. The catalyst system according to claim 1, wherein the active material of the catalyst in the last catalyst zone towards the reactor outlet has an antimony content (calculated as antimony trioxide) between 1.2 to 1.6 wt. %.

14. The process according to claim 8, wherein the active material of the catalyst in the last catalyst zone towards the reactor outlet has an antimony content (calculated as antimony trioxide) between 1.0 to 1.8 wt. %.

15. The process according to claim 8, wherein the active material of the catalyst in the last catalyst zone towards the reactor outlet has an antimony content (calculated as antimony trioxide) between 1.1 to 1.7 wt. %.

16. The process according to claim 8, wherein the active material of the catalyst in the last catalyst zone towards the reactor outlet has an antimony content (calculated as antimony trioxide) between 1.2 to 1.6 wt. %.

17. A process for gas phase oxidation in which a gas stream comprising at least one hydrocarbon and molecular oxygen is passed through the catalyst system according to claim 1.

18. A process for gas phase oxidation in which a gas stream comprising at least one hydrocarbon and molecular oxygen is passed through the catalyst system according to claim 13.

19. The catalyst system according to claim 1, wherein the catalyst is applied to an inert carrier in one or more shells.

* * * * *